(12) United States Patent
Wang et al.

(10) Patent No.: US 8,383,378 B2
(45) Date of Patent: Feb. 26, 2013

(54) MICRO-BUBBLE PLATE FOR PATTERNING BIOLOGICAL AND NON-BIOLOGICAL MATERIALS

(75) Inventors: Yuli Wang, Irvine, CA (US); Mark Bachman, Irvine, CA (US); Christopher E. Sims, Irvine, CA (US); Guann-Pyng Li, Irvine, CA (US); Nancy Allbritton, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 638 days.

(21) Appl. No.: 11/539,695

(22) Filed: Oct. 9, 2006

(65) Prior Publication Data
US 2007/0128716 A1     Jun. 7, 2007

Related U.S. Application Data

(60) Provisional application No. 60/725,219, filed on Oct. 10, 2005.

(51) Int. Cl.
| | | |
|---|---|---|
| *C12N 11/02* | (2006.01) | |
| *C12Q 1/68* | (2006.01) | |
| *C12M 1/34* | (2006.01) | |

(52) U.S. Cl. ..... 435/174; 435/177; 435/180; 435/287.2; 435/288.5; 530/812; 530/813; 422/407; 422/552

(58) Field of Classification Search .................. None
See application file for complete search history.

(56) References Cited

U.S. PATENT DOCUMENTS

| | | | |
|---|---|---|---|
| 5,368,634 A * | 11/1994 | Hackett | 95/260 |
| 5,998,129 A * | 12/1999 | Schutze et al. | 435/4 |
| 6,180,239 B1 | 1/2001 | Whitesides et al. | |
| 6,646,238 B1 * | 11/2003 | Fuhr et al. | 219/521 |
| 2001/0038449 A1 * | 11/2001 | Baer et al. | 356/244 |
| 2001/0055882 A1 * | 12/2001 | Ostuni et al. | 438/694 |
| 2002/0119578 A1 | 8/2002 | Zaffaroni et al. | |
| 2004/0053403 A1 | 3/2004 | Jedrzejewski et al. | |
| 2004/0067596 A1 | 4/2004 | Halverson et al. | |
| 2004/0171135 A1 * | 9/2004 | Ostuni et al. | 435/283.1 |
| 2006/0013031 A1 * | 1/2006 | Ravkin et al. | 365/63 |
| 2006/0121500 A1 * | 6/2006 | Bachman et al. | 435/6 |

FOREIGN PATENT DOCUMENTS

| | | |
|---|---|---|
| EP | 1365014 A1 | 11/2003 |
| FR | 2848477 A1 | 6/2004 |

OTHER PUBLICATIONS

EP, Supplementary European Search Report, EP 06 85 0517, Mar. 24, 2011.

* cited by examiner

*Primary Examiner* — P. Kathryn Wright
(74) *Attorney, Agent, or Firm* — Dickstein Shapiro LLP; Kenneth S. Roberts

(57) ABSTRACT

Systems and methods are provided for patterning biological and non-biological material at specific sites on a plate, as well as growing three dimensional structures. Preferred embodiments comprise a plate with regions that will trap gas, usually in the form of bubbles, when the plate is submerged in liquid. Other embodiment of the present invention include a method for placing materials on the plate at pre-determined locations through the use of trapped gas to prevent materials from collecting at unwanted regions. The plate has great utility for plating cells and tissues at specific sites, such as on an array. The disclosed method can also be used to coat the surface of a plate with coatings at specific locations for patterned coating applications and to build up materials to produce three dimensional structures, including micro-mechanical structures—where the structures may be formed from living or non-living material, tissue or non-tissue, organic or inorganic, and the like.

12 Claims, 3 Drawing Sheets

MICRO-BUBBLE PLATE FOR PATTERNING BIOLOGICAL AND NON-BIOLOGICAL MATERIALS

CROSS-REFERENCE TO RELATED APPLICATION

This application claims the benefit of U.S. Provisional Application No. 60/725,219, filed Oct. 10, 2005 which application is incorporated herein by reference.

FIELD

The present invention relates to biochemical analysis and, more particularly, to a micro-bubble plate for patterning biological and non-biological materials.

BACKGROUND

The ability to pattern cells, tissues, organisms, colonies, embryos, and other biological material, as well as non-biological material, at specific sites on a plate is important for many areas of scientific research and medicine. By placing such materials at known locations, researchers may study many samples under identical and controlled conditions, while monitoring each sample independently and repeatedly over time. Since each sample is in a known location, large numbers of samples may be studied, resulting in statistically significant data sets. Arrays of isolated biological media can be used to assist in diagnosis by observing the media under controlled conditions in the presence of unknown agents or pathogens.

To accomplish patterning of media, conventional technologies rely on three major strategies: (1) patterned surface treatments, (2) structured microwells, (3) physical stenciling, all of which have shortcomings overcome by this invention.

Patterned surface treatments create surfaces with specific chemistry at predetermined locations. This is performed by lithographic methods (i.e., UV radiation through a photographic mask), or by rubber stamp approaches, where chemicals are physically transferred to the plate surface by a patterned rubber stamp. The result of surface treatments is that regions are made favorable or unfavorable for media attachment (e.g., cell growth, protein binding). After incubation with the media, the media and buffer are washed away. These methods are not highly selective—patterning of the media is not particularly good, and each media/plate requires a different surface treatment specific to that media/plate combination.

Structured microwells may be patterned into the surface by lithographic etching or molding cavities in the surfaces. Such microwells are of limited use because cells will readily grow out of the cavities and media may readily coat all sides of the microwells. For best results, high aspect ratio wells are required (to contain the biological media), increasing manufacturing difficulty and cost.

Physical stenciling techniques use a rigid temporary barrier that is placed over the plate of interest. This barrier is in the form of a stencil or microfluidic device. Following this, media is introduced and allowed to attach to the surface at locations allowed by the stencil. After attachment, the stencil is removed leaving patterned media. This method suffers because it is difficult (and expensive) to produce stencils of high resolution, with large numbers of precision holes. The stencils must remain in intimate contact with the surface during the entire period of incubation (attachment). Generally, stencils leak between openings further reducing pattern resolution. Finally, such stencils are expensive, and a single stencil must be used for the entire incubation period for each surface that is to be patterned.

Therefore, improved methods and systems for patterning biological and non-biological material on specific sites on a plate would be desirable.

SUMMARY

The various embodiments and examples provided herein are generally directed to systems and methods for patterning biological and non-biological material at specific sites on a plate, as well as growing or building three dimensional structures from this material. Preferred embodiments comprise a plate with regions that will trap gas, usually in the form of bubbles, when the plate is submerged in liquid. Other embodiment of the present invention include a method for placing materials on the plate at pre-determined locations through the use of trapped gas to prevent materials from collecting at unwanted regions. The plate has great utility for plating cells and tissues at specific sites, such as on an array. The disclosed method can also be used to coat the surface of a plate with coatings at specific locations for patterned coating applications and to build up materials to produce three dimensional structures, including micro-mechanical structures—where the structures may be formed from living or non-living material, tissue or non-tissue, organic or inorganic, and the like.

The trapped gas cavities or troughs are used to facilitate patterning of biological media and non-biological media, which may advantageously be in array or at addressable and/or removable sites. Gas bubbles preferably provide contiguous, impenetrable barriers to cell and media attachment on the surfaces of the cavities, i.e., the dry regions, effectively isolating specific location or sites, i.e. "wet regions", from one another on the plate where it is desirable for cell and media to attach. The gas bubbles can be made very easily using hydrophobic or liquid repellant cavities, even for extremely small cavities with width or diameter dimensions of less than a micrometer. The gas bubbles preferably extend beyond the opening of the cavities and above the wet regions, but may extend up to or just below the wet regions. Gas bubble formation advantageously requires no external handling or manipulation, does not damage or impede biological function, and can be removed easily at any time.

The gas bubbles can also be used to provide temporary scaffolding for tissue growth or growth or formation of non-tissue structures. Conventional methods use biodegradable polymer scaffolds that are eroded away over time to release tissue structures. Gas bubbles provide a cheap, convenient, simple method for creating temporary 3-D scaffolding structures for micromachining and tissue engineering applications Further, objects and advantages of the invention will become apparent from the following detailed description.

DETAILED DESCRIPTION OF THE PREFERRED EMBODIMENTS

Each of the additional features and teachings disclosed below can be utilized separately or in conjunction with other features and teachings to provide a micro-bubble plate for patterning biological and non-biological materials. Representative examples of the present invention, which examples utilize many of these additional features and teachings both separately and in combination, will now be described in further detail with reference to the attached drawings. This detailed description is merely intended to teach a person of skill in the art further details for practicing preferred aspects of the present teachings and is not intended to limit the scope of the invention. Therefore, combinations of features and steps disclosed in the following detail description may not be necessary to practice the invention in the broadest sense, and are instead taught merely to particularly describe representative examples of the present teachings.

Moreover, the various features of the representative examples and the dependent claims may be combined in ways that are not specifically and explicitly enumerated in order to provide additional useful embodiments of the present teachings. In addition, it is expressly noted that all features disclosed in the description and/or the claims are intended to be disclosed separately and independently from each other for the purpose of original disclosure, as well as for the purpose of restricting the claimed subject matter independent of the compositions of the features in the embodiments and/or the claims. It is also expressly noted that all value ranges or indications of groups of entities disclose every possible intermediate value or intermediate entity for the purpose of original disclosure, as well as for the purpose of restricting the claimed subject matter.

The various embodiment provided herein are generally directed to systems and methods for patterning biological and non-biological material at specific sites on a plate. A preferred embodiment comprises a plate composed of regions containing surfaces where liquid is intended to make contact (wet regions) and other regions where liquid is not intended to make contact (bubble or dry regions), which preferably surround and isolate the wet regions. This is made possible by the use of structured material to produce contiguous air or gas filled regions at specific or known locations. In use, the plate makes possible the patterning of biological material, cells or small living organisms at predetermined locations, directing tissue growth, depositing inorganic and organic material at predetermined locations, localizing chemical reactions, and patterning coatings.

Figure 1:
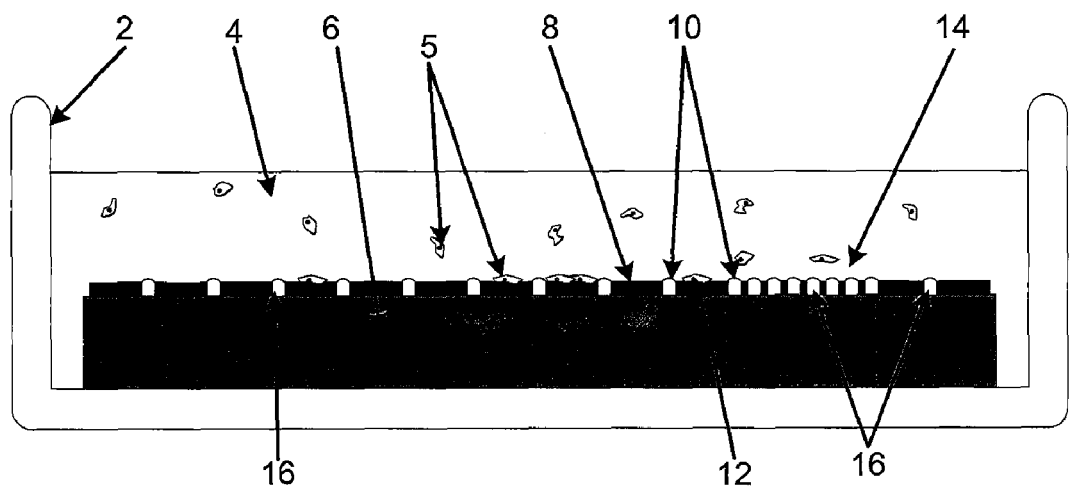
FIG. 1 is a schematic cross sectional view of a bubble plate submerged in a container within a solution containing material of interest.

Referring to FIG. 1, a container 2 is filled with a solution 4 containing materials 5 of interest, in this instance cells. As depicted, a plate 6 is placed in the liquid filled container 2. Regions on the plate 6 are fabricated containing surfaces 8 at different elevations, the "wet regions", at which the material of interest 5 comes into contact with and adheres to the plate 6. Cavities, troughs or gaps 16, i.e., the "dry regions", are preferably formed in the plate 6 and made to be hydrophobic or liquid repellant, and thus trap gas bubbles 10 that form a contiguous, impenetrable barrier to the material of interest 5. The bubbles 10 preferably extend beyond the opening of the cavities 16 and above the wet regions 8, but may extend up to or just below the wet regions 8 to prevent attachment of material 5 on the dry regions 16.

Figure 2:
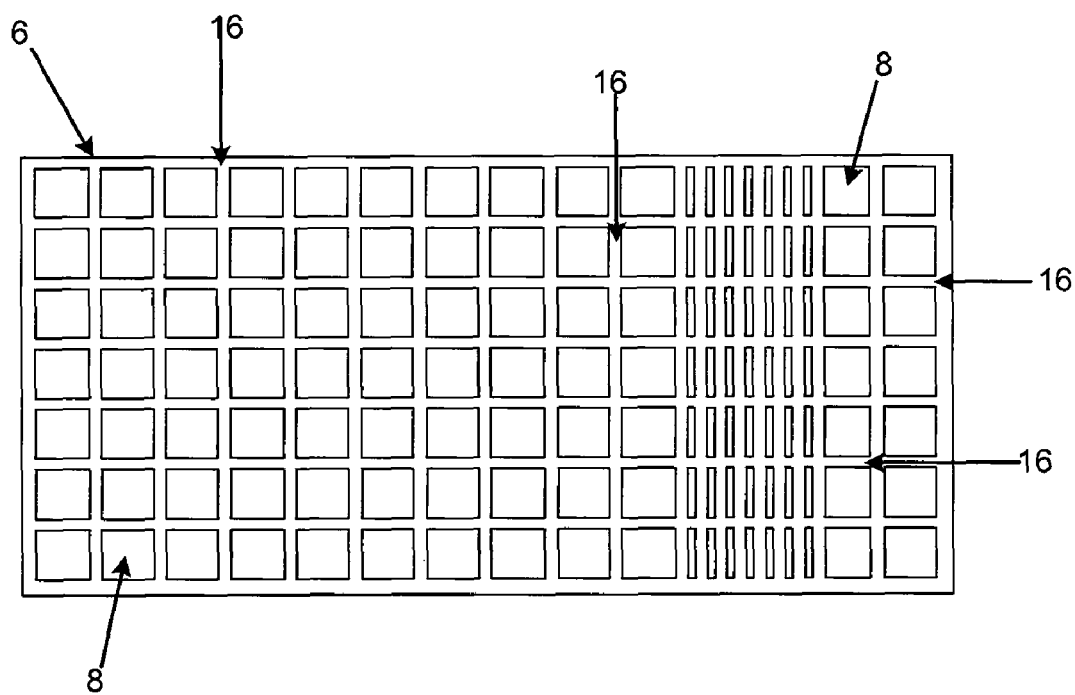
FIG. 2 is a schematic top view of the bubble plate shown in FIG. 1.
Figure 3:
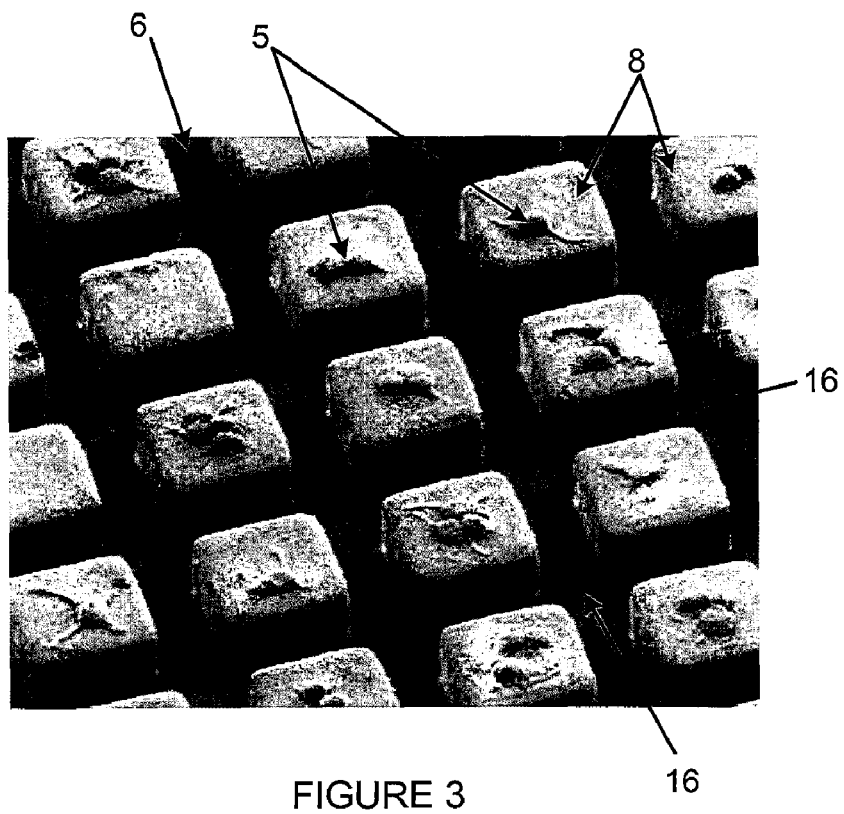
FIG. 3 is a photograph showing cells patterned on elevated surfaces of the bubble plate using the preferred method described herein.

As depicted in FIGS. 2 and 3, the cavities or troughs 16 preferably run contiguously across the plate 6 criss-crossing one another to isolate the wet regions, i.e., raised surfaces 8. The wet regions 8 can be patterned into an array with each region or location being addressable. Regions 14 containing many bubbles 10, as depicted in FIG. 1, can be generated by producing a large numbers of cavities 16 in close concentration.

In operation, materials 5 from the solution 4, e.g., cells, sink and land on the plate 6. If the cells 5 land on exposed surfaces 8 they may stick or react with the surface at that point 12. If they land on bubbles 10, they do not stick, but typically slide over to the exposed plate regions 8. If they land on regions 14 containing many bubbles 10, they will float on the surface of the bubbles 10, but will not adhere to the plate 6.

The liquid repellency of the bubble regions 14 may be enhanced by the use of plate material or surface treatments that make the bubble regions hydrophobic (e.g., for water), lipophobic (e.g., for oil), or otherwise repellant to the liquid. The simplest way to enhance stable bubble formation is to generate small cavities that trap gas. Gas-trapping cavities 16 should be constructed of hydrophobic materials, or treated to be hydrophobic. Methods for making regions hydrophobic or hydrophillic vary and can include LW grafting, coatings applied by non-selective treatment as through a stencil, coatings applied by selective treatment such as silane which forms naturally on one material but not another, or imparted naturally by choice of material, i.e., glass surface versus plastic surfaces.

After submerging the plate 6 in liquid 4, or adding liquid 4 over the surface of the plate 6, the hydrophobic cavities 16 will create trapped gas bubbles 10. Flat or wetting surfaces 8 will not repel liquid and these surfaces 8 will remain in contact with the liquid 4. By appropriately arranging the cavities 16, gas regions 14 of arbitrary shape and size can be prepared.

The stability of the gas bubbles depends on the surface tension of the liquid that coats the plate, as well as the shape and size of the gaps or cavities. Bubbles form due to surface tension which prevents liquid from flowing into the gaps. As the liquid flows over the plate, the leading edge of the liquid has a surface minuscus (like a "skin") that cannot enter the gaps or cavities. The surface tension also applies when the liquid is sitting on top of the gap or cavities. However, large cavities are generally less stable and hence less likely to form gas bubbles. Typical cavities for bubble regions preferably range from 50 nanometers to 500 micrometers. Deep cavities produce the most stable bubbles. Furthermore, these bubbles may be made to grow or shrink, depending on the temperature and pressure of the liquid. Bubbles can be re-absorbed into solution by applying pressure, typically several atmospheres, to the solution.

The plate can be produced by a variety of manufacturing methods. In one embodiment, a plate is prepared from plastic. Small cavities are embossed into the surface of the plastic by pressing a heated mold containing the relief pattern against the polymer. When the metal is removed, the plastic surface will contain structures that mirror the features in the metal mold. If desired, an additional surface treatment, such as UV grafting or other methods noted above, may be applied to make the highest surfaces hydrophilic or compatible with cell growth. This plate will thus contain regions where gas cavities will form, and regions where liquid will come in direct contact with the surface. In addition to the embodiment described above, there are many methods available for building the plate including building patterned regions over the surface, etching cavities into the surface, casting, molding, micro-machining, and the like. The cavities can be of any shape, size, and depth provided that it can generate a stable region of air or gas. For example, tiny "hairs" of micrometer or nanometer scale may be used to generate large regions of trapped air or gas.

The method of the preferred embodiment can enable the patterning of cells or other living creatures at specific isolated sites on the plate. The method is as follows. First, a plate 6 is prepared containing wet (or material retention) regions 8 and bubble (or material deterrent) regions 14 by any suitable manufacturing process, such as the manufacturing process previously described. Next, the plate 6 is placed in solution 4 containing material of interest 5 such as cells in suspension. The cavities 16 in the bubble regions 14 form gas bubbles 10 that coat the region 14 with gas, isolating the wet regions 8 which are not coated with gas. After some time, the cells 5 sink to the plate 6. Cells 5 that fall on bubbles 10 will not be able to adhere to the surface 8. Cells that fall on wetted surfaces 8 will be able to adhere and grow. After a suitable period of time, the solution 4 is washed and replaced with clean buffer. Cells 5 that have adhered to the surface 8 will remain, whereas cells 5 that were left on bubble regions 14 will be removed. Thus, the resulting plate 6 will contain cells 5 in a patterned formation on the raised surfaces 8 as depicted in the photograph shown in FIG. 3.

Turning to FIG. 3, the photograph shows cells 5 patterned on elevated surfaces 8 of a plate using the method described above. There are no cells in the cavities 16 between the elevated regions 8 because they were protected by gas bubbles. If the preferred method had not been used, fewer than 1% of the elevated surfaces would have cells plated on them and the location of cells would be randomly distributed in the regions between the elevated surfaces.

The method discussed herein can enable the use of cells or other living creatures to create three dimensional structures which can be useful for micromechanical applications, or for generating complex tissue structures. In this embodiment, cells are grown to confluence. Upon further growth, cells extend over the bubbles to form bridging structures. The trapped gas may be chosen to enhance a particular feature of the cell growth, or to produce a desired growth property. When the bubbles are removed, the cells that remain form a living 3-D tissue structure.

Figure 4:
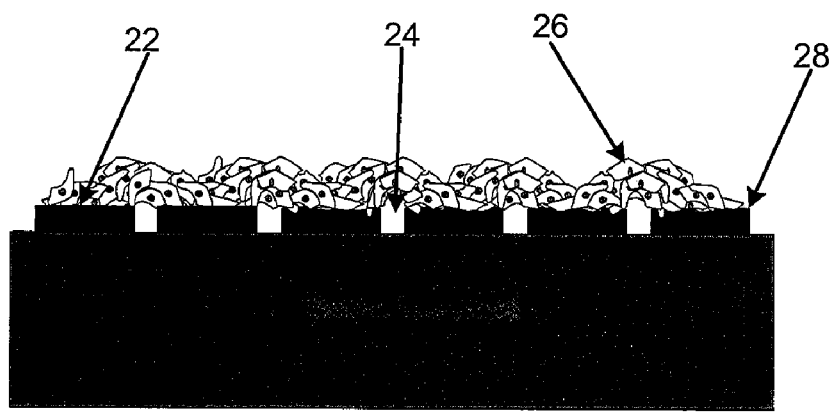
FIG. 4 is a schematic cross-sectional view of the bubble plate showing how 3-D structures can be built from cells using gas bubbles as temporary scaffolding.

Referring to FIG. 4, a diagram is produced that shows how 3-D structures can be built from cells using gas bubbles. As cells grow beyond confluence, they form bridges over the bubbles that result in three dimensional structures when the bubbles are removed. Elevated surfaces 22 are prepared that promote cell growth. Gas bubbles provide openings 24 that cells must bridge. Resulting tissue structure is a bridged tissue 26 that spans the spaces 24 between the elevated surfaces 28.

Figure 5:
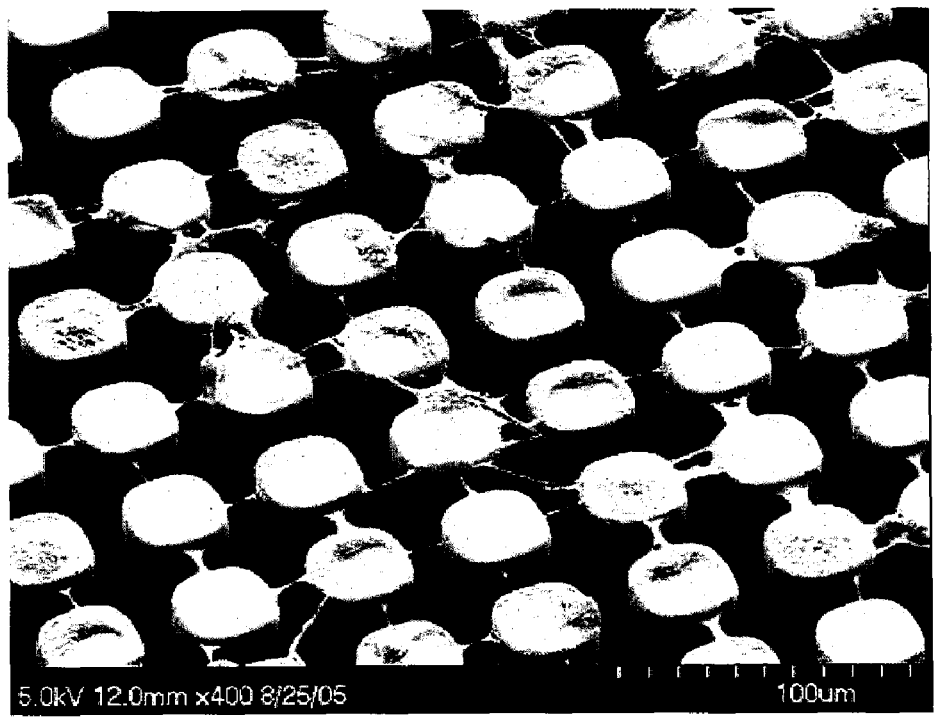
FIG. 5 is a photograph showing cells patterned on elevated surfaces of the bubble plate and extending over the cavities of the plate using the preferred method described herein.

Turning to FIG. 5, a photograph is provided that shows cells patterned on elevated surfaces of a plate using the method described above. In this image, cells are seen to grow over the air or gas gaps, creating three-dimensional structures.

Cell fixation methods can be used to cross-link the molecules in the living 3-D tissue structures to produce hardened structures. In addition, chemical additives, such as monomers may be added to the tissues, then polymerized or hardened, to make stronger features, or features with specific mechanical, optical or electrical properties. This method allows one to use living organisms to build structures that are then converted into non-living structures.

Non-living materials, both organic and inorganic, may also be patterned in this manner. While in solution, chemicals, compounds, nanoparticles, or other materials may be precipitated out to form layers on the surface. The bubble regions serve to protect regions of the plate, whereas non-bubble regions may allow the precipitants to stick, forming patterned regions. If the deposited layers are thick enough, they may form three dimensional structures over the bubbles. Other methods of depositing materials on the surface, such as physical adsorption, chemical reactions, UV grafting, etc., may all be patterned by this technique. Furthermore, the gas in the cavities may be chosen to produce a preferred chemical reaction with the liquid.

Figure 6:
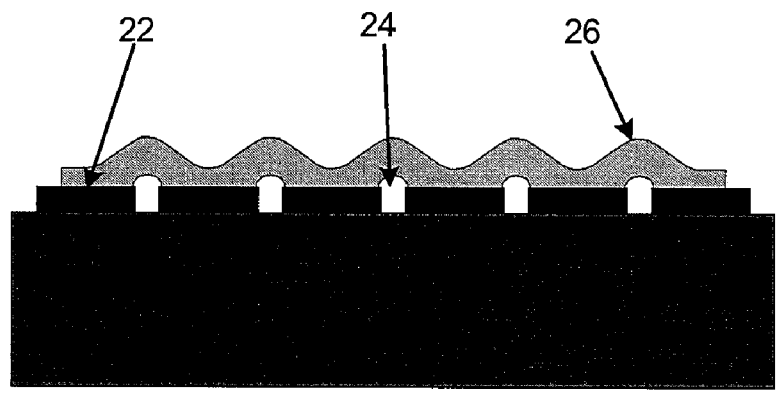
FIG. 6 is a schematic cross sectional view of the bubble plate showing how 3-D structures can be built from chemical materials, precipitates, polymers, and the like using the gas bubbles as temporary scaffolding.
Figure 7:
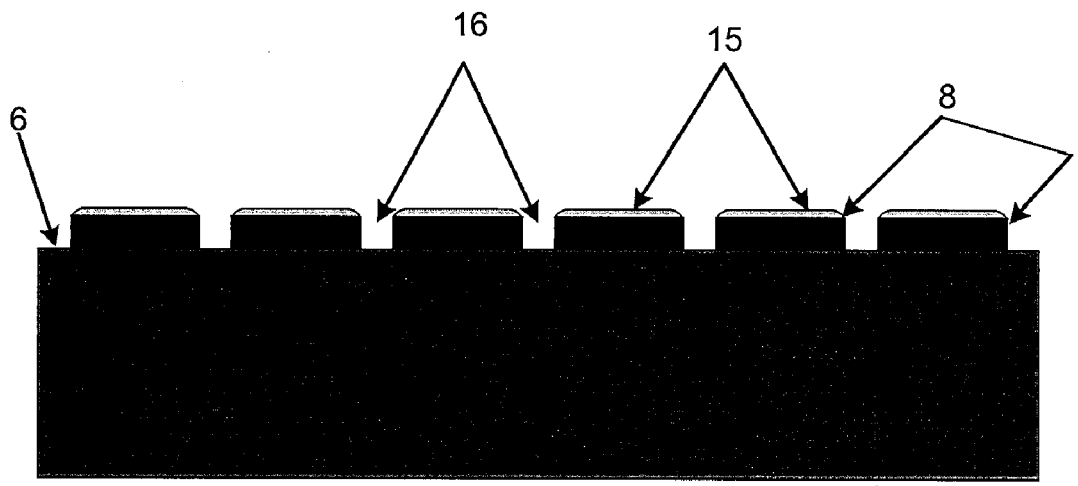
FIG. 7 is a schematic cross sectional view of the bubble plate showing coating material patterned on elevated surfaces of the bubble plate using the preferred method described herein.

Referring to FIG. 6, a diagram is provided that shows how 3-D structures can be built from chemical materials, precipitates, polymers, etc. Materials are deposited over the bubbles and adhere to the elevated surfaces 22. Bubbles prevent materials from adhering to cavities 24. If the deposition is thick enough, resulting structure has bridging structures 26. In the event that the gas reacts with the liquid, solidification may occur due to the presence of the gas. If bridging does not occur, the result is a patterned deposition of material 15, e.g., electroplating metal, on top of the elevated surfaces 8 as shown in FIG. 7. The patterned deposition method described herein can be used to form a patterned deposition on the surfaces of removable pallets as described in U.S. Patent Application Publication No. 2006/0121500 and U.S. Provisional Application No. 60/746,008, which applications are incorporated herein by reference.

These embodiments are meant to be illustrative examples and not exhaustive of the types of useful devices that can be built by patterning gas cavities on a plate. The plate and method discussed above will have great utility for a variety of applications including, but not limited to: (1) cellular assays, particularly for arrays, (2) tissue engineering, (3) micromechanical fabrication.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed:

1. A method of patterning of biological materials of interest at specific sites on a plate, the materials of interest comprising cells, tissues, DNA or living organisms, the method comprising the steps of submerging a plate having a body in a solution containing a biological material of interest in suspension, the biological material of interest including one of cells, tissues, DNA and living organisms, the plate including a plurality of elevated sites extending from a surface of the body and a plurality of troughs extending contiguously across the body in a crisscrossing configuration separating each of the plurality of elevated sites from one another, forming a contiguous gas bubble within the plurality of troughs, the contiguous gas bubble isolating each of the plurality of elevated sites from one another, and adhering the biological material of interest to a top surface of the plurality of elevated sites on the body of the plate, wherein the contiguous gas bubble preventing the biological material of interest from adhering to surfaces within the plurality of troughs, and releasing one or more of the plurality of elevated sites from the plate with biological material of interest adhered to the top surface of the released one or more of the plurality of elevated sites, wherein the released one or more of the plurality of elevated sites acting as a carrier for the biological material of interest adhered thereto, and wherein the plurality of elevated sites are attached to and extending up from the body of the plate and the nature of the attachment of the plurality of elevated sites to the body of the plate is releasable leaving the structure of the body of the plate intact when one or more of the plurality of elevated sites is released from the body of the plate.

2. The method of claim 1 wherein the step of forming a contiguous gas bubble includes, as the plate is submerged in a liquid, the step of trapping the gas in the plurality of troughs formed between the plurality of elevated sites.

3. The method of claim 2 wherein the surfaces of within the plurality of troughs are liquid repellant.

4. The method of claim 2 wherein the surfaces of within the plurality of troughs are hydrophobic.

5. The method of claim 2 wherein the top surfaces of the plurality elevated sites are hydrophillic.

6. The method of claim 2 wherein the step of releasing one or more of the plurality of elevated sites from the plate includes applying an energy pulse to the one or more of the plurality of elevated sites to release the one or more of the plurality of elevated sites from the plate.

7. The method of claim 6 wherein the energy pulse is a laser pulse.

8. The method of claim 1 further comprising the step of forming a plurality of bridges out of the biological material of interest over the plurality of troughs.

9. The method of claim 8 wherein the biological material of interest is one of a living cell, living cells, living tissue, a living organism and living organisms, and the step of forming a bridge includes growing the biological material of interest over the plurality of troughs.

10. The method of claim 9 further comprising the step of converting the living cell, living cells, living tissue, a living organism and living organisms into a non-living cell, non-living cells, non-living tissue, a non-living organism and non-living organisms.

11. The method of claim 9 further comprising the step of adding monomers to the biological material of interest and polymerizing the monomer composite material.

12. The method of claim 1 further comprising the step of forming a three dimensional structure by bridging the plurality of troughs with the biological material of interest.

* * * * *